(12) United States Patent
Petitdidier et al.

(10) Patent No.: US 8,152,364 B2
(45) Date of Patent: Apr. 10, 2012

(54) METHOD FOR MEASURING THE CREEP OF A THIN FILM INSERTED BETWEEN TWO RIGID SUBSTRATES, WITH ONE CANTILEVER END

(75) Inventors: Cecile Petitdidier, Beacon, NY (US); Raluca Tiron, Saint Martin d'Heres (FR); Benedicte Mortini, Meylan (FR)

(73) Assignee: Commissariat a l'Energie Atomique, Paris (FR)

( * ) Notice: Subject to any disclaimer, the term of this patent is extended or adjusted under 35 U.S.C. 154(b) by 585 days.

(21) Appl. No.: 12/314,746

(22) Filed: Dec. 16, 2008

(65) Prior Publication Data

US 2009/0260450 A1 Oct. 22, 2009

(30) Foreign Application Priority Data

Dec. 20, 2007 (FR) ...................................... 07 08955

(51) Int. Cl.
*G01N 25/00* (2006.01)
*G01N 3/00* (2006.01)
(52) U.S. Cl. .............................. 374/45; 374/51; 374/102
(58) Field of Classification Search ..................... 374/45, 374/121, 52, 102, 47
See application file for complete search history.

(56) References Cited

U.S. PATENT DOCUMENTS

| | | | | |
|---|---|---|---|---|
| 2,670,624 A * | 3/1954 | Faris, Jr. et al. | ................. | 374/52 |
| 5,154,085 A * | 10/1992 | Takeda | ............................. | 374/47 |
| 5,184,517 A * | 2/1993 | Kelzer | ............................. | 73/851 |
| 5,187,987 A * | 2/1993 | Anderson et al. | ................ | 73/852 |
| 5,199,305 A * | 4/1993 | Smith et al. | ...................... | 73/851 |
| 5,710,426 A | 1/1998 | Reed et al. | | |
| 5,915,283 A | 6/1999 | Reed et al. | | |
| 6,386,045 B1 | 5/2002 | Nakamura et al. | | |
| 6,916,116 B2 * | 7/2005 | Diekmann et al. | ............. | 374/102 |
| 7,543,507 B2 * | 6/2009 | Li et al. | ............................ | 73/851 |
| 7,716,987 B2 * | 5/2010 | Sathish et al. | ................... | 73/589 |
| 2003/0214997 A1* | 11/2003 | Diekmann et al. | ............. | 374/102 |
| 2009/0260450 A1* | 10/2009 | Petitdidier et al. | .............. | 73/841 |

FOREIGN PATENT DOCUMENTS

EP  0 793 088 B1  8/2003

OTHER PUBLICATIONS

Carlier et al.; "Supported dynamic mechanical thermal analysis: an easy, powerful and very sensitive technique to assess thermal properties of polymer, coating and even nanocoating", Polymer, vol. 42, No. 12, 2001, pp. 5327-5335.

Haque et al, "Application of MEMS force sensors for in situ mechanical characterization of nano-scale thin films in SEM and TEM", Sensors and Actuators, vol. 97-98, 2002, pp. 239-245.

\* cited by examiner

*Primary Examiner* — Yaritza Guadalupe-McCall

(74) *Attorney, Agent, or Firm* — Oliff & Berridge, PLC

(57) ABSTRACT

A film is inserted between two rigid substrates which form a sample. The sample is fixed at a first end in a device for measuring creep. The device comprises means for applying a predetermined force on a free end of the sample. The film being sheared, study of its creep can be performed.

12 Claims, 1 Drawing Sheet

METHOD FOR MEASURING THE CREEP OF A THIN FILM INSERTED BETWEEN TWO RIGID SUBSTRATES, WITH ONE CANTILEVER END

BACKGROUND OF THE INVENTION

The invention relates to a method for measuring the viscoelastic properties of a film inserted between two rigid substrates forming a sample comprising a first end fixed in a measuring device, the method comprising application of a force on a predetermined area of the sample.

STATE OF THE ART

Study of the viscoelastic properties of materials and in particular of the creep is commonly performed by means of dynamic mechanical analysis (DMA) equipment. The document EP-B-0793088 describes a dynamic mechanical analysis device that can be used for characterizing the viscoelastic properties of a large number of materials.

This type of device enables multiple stresses to be applied to different samples, for example 3-point flexure tests or single/double cantilever flexure tests. The sample is then patterned so as to form a test tube with dimensions compatible with the object of the study. The test tube is then subjected to stresses, and measurement of resulting strains and deformations enable viscoelastic characterization thereof, and in particular enable its creep to be determined.

However these methods are suitable for fairly thick samples, typically with a thickness ranging from a few microns to a few millimeters, which are solid at ambient temperature and not brittle.

Thus, at ambient temperature, glass materials with a low mechanical strength, materials having a lower vitreous transition temperature than the ambient temperature, and materials in liquid state are not analyzable.

The article by Carlier et al. "Supported dynamic mechanical analysis: an easy, powerful and very sensitive technique to assess thermal properties of polymer, coating and even nanocoating", Polymer (42), pp 5327-5335, 2001, describes (FIG. 1) the use of a device for measuring the viscoelastic properties of a set of polymer resin films 2, inserted between two rigid plates 3 (FIG. 2) to form a sample 1. Sample 1 is secured by clamps 4 at each of the ends thereof, thereby constituting a double cantilever flexure assembly. It is stressed by means a periodic force applied between the two clamps and illustrated by arrows in FIG. 1. With this assembly, most of the viscoelastic properties of film 2 are accessible for measurement. However, although film 2 is sheared, it is impossible to measure the creep of the resin film correctly. In the measured signal, the rigid plates do in fact have a majority effect compared with the resin, which makes measurement impossible or incorrect. Moreover, the stack comprises a very large number of substrates so as to increase the quantity of material and thereby obtain a measurable signal.

OBJECT OF THE INVENTION

The object of the invention consists in providing a method for measuring the creep whereby the creep characteristics of a thin film can be measured, measurement being quick and easy to implement;

The method according to the invention is characterized in that said force is applied on a free end of the sample and the method comprises measuring the creep of the film and determining a characteristic temperature of the film.

BRIEF DESCRIPTION OF THE DRAWINGS

Other advantages and features will become more clearly apparent from the following description of a particular embodiment of the invention given for non-restrictive example purposes only and represented in the accompanying drawings, in which.

DESCRIPTION OF A PREFERRED EMBODIMENT OF THE INVENTION

Figure 1:
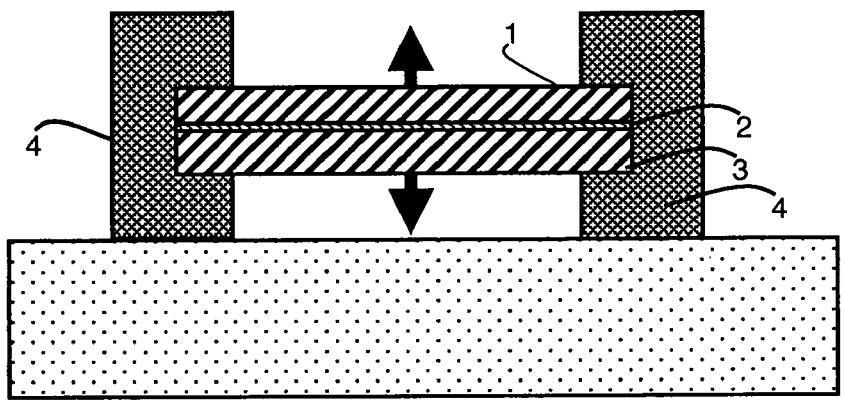
FIG. 1 represents a schematic cross-sectional view of a device according to the prior art.
Figure 2:
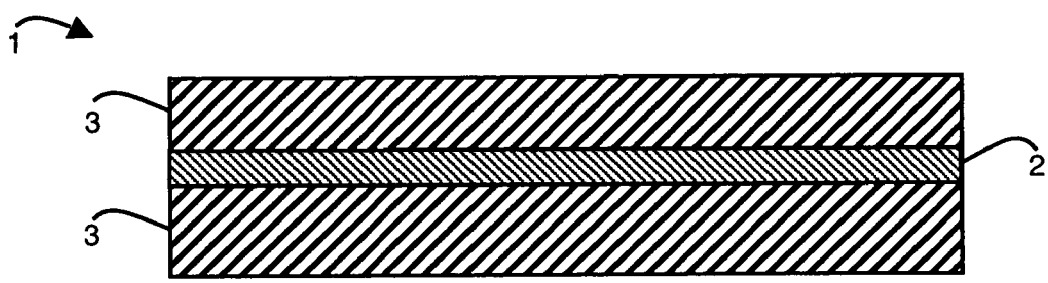
FIG. 2 represents a schematic cross-sectional view of a sample according to the prior art.
Figure 3:
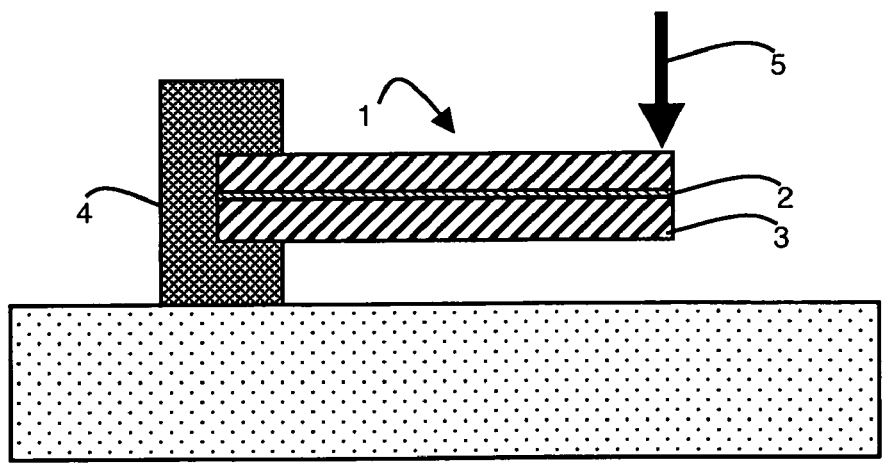
FIG. 3 represents a schematic cross-sectional view of a device according to the invention.

As illustrated in FIG. 3, sample 1 to be analyzed is formed by a thin film 2 to be characterized, inserted between two rigid substrates 3. Substantially parallel top and bottom rigid substrates 3 are advantageously chosen made from the same material to facilitate analysis of the viscoelastic properties of thin film 2. Thin film 2 preferably has a thickness of less than 1 μm which means that it cannot be held at its ends without being deformed. Rigid substrates 3 are chosen inert in the temperature range in which sample 1 is stressed. Substrates 3 are moreover sufficiently flexible, resilient, to withstand deformation of thin film 2. Sample 1 is advantageously in the shape of a rectangular parallelogram whose length is substantially greater than the width and height. For example, sample 1 has a length of 3.5 cm with a width of 1.5 cm, its thickness preferably being between 0.1 and 1 mm with substrates with a thickness of 750 μm.

Film 2 is for example a lithographic resin with a thickness comprised between a few tenths of a nanometer and one millimeter, typically between 1 mm and 0.1 nm. Rigid substrates 3 are advantageously made of silicon, for example bulk silicon substrates.

Film 2 is deposited on one of rigid substrates 3 by any suitable technique, for example by spin coating, and second rigid substrate 3 is then deposited on film 2.

Sample 1 is fixed at one end only by any suitable fixing means, and thus presents a fixed end and a free end. The sample is then substantially horizontal, in an unstressed state, i.e. in the sample, the stack of rigid substrates and study film 2 is vertical.

Sample 1 is advantageously clamped at its fixed end by a rigid clamp 4 which acts as cantilever. The other end, which is free, is then subjected to means for applying a force resulting in application of a vertical force schematically represented by arrow 5 in FIG. 3. The force to be applied further depends on the substrate and not on film 2. This case is then analogous to that of a homogenous beam clamped at one end and studied in flexure. When the polymer layer reaches its glass transition temperature, its elastic properties change and it shears, which enables it to follow the deformation of the substrate.

Shearing of film 2 causes vertical displacement of the free end of substrate 3 and variation of this displacement with the temperature of the sample allows the different thermal events (glass transition, decomposition, cross-linking, polymerization . . . ) of thin film 2 to be determined.

A study at constant temperature enables the creep properties of the thin film to be measured along with study of the variation of displacement of the substrates with time. In this way, characteristic creep times and creep amplitudes are determined.

In the case where the film is a photoresist resin, it is also possible to study the chemical reactions that are conventionally used during its life cycle (cross-linking, degradation, polymerization, and so forth).

Rigid clamp 4 is typically a clamp used in single or double cantilever flexure testing, and application of the stress can for example be performed by the same type of device as in the case of 3-point flexure stressing.

The device described above is more particularly suitable for studying creep of a film 2 formed by a lithographic resin but the device is, in a more general manner, suitable for studying the creep of vitreous materials having a low mechanical strength at the stress temperature. Film 2 can for example be made from a material having a glass transition temperature lower than the stress temperature.

Device 2 can be used for example for studying the variations of a characteristic temperature, for example the glass transition temperature, versus the thickness of thin film 2. Study of the variations of the glass transition temperature can be performed in the following manner:

application of a predetermined force to a free end of sample 1, measuring film 2, determining the creep of the film 2 from the shear measurement.

The substrate being in flexure, measurement of the displacement of the ends of the substrates is performed versus the temperature variations. It is also possible to apply a strain and to measure the force necessary to maintain this strain. The forces involved are typically a few Newtons. The temperature variation can be achieved simply by applying a temperature ramp.

The invention claimed is:

1. A method for measuring the viscoelastic properties of a sample film comprising:
   inserting the sample film between two rigid substrates, the sample film having a first end and a free end, the first end being fixed in a measuring device;
   applying a force on the free end of the sample film;
   measuring a creep of the sample film; and
   determining a characteristic temperature of said sample film.

2. The method according to claim 1, further comprising cantilevering of the first end of the sample film by means of a clamp.

3. The method according to claim 1, wherein the sample film has a thickness between 1 mm and 0.1 nm.

4. The method according to claim 1, wherein the two rigid substrates are made from silicon.

5. The method according to claim 1, wherein the sample film is a lithographic resin.

6. The method according to claim 1, wherein the step of inserting the sample film between two rigid substrates includes inserting the sample film so that an area of each of the two rigid substrates that is in contact with the sample film is substantially identical.

7. A method for measuring a glass transition temperature of a sample film comprising:
   inserting the sample film between two rigid substrates, the sample film having a first end and a free end, the first end being fixed in a measuring device;
   applying a force on the free end of the sample film;
   measuring a shear of the sample film;
   determining a creep of the sample film based on the shear measurement; and
   determining a glass transition temperature of the sample film.

8. The method according to claim 7, further comprising
   providing a plurality of sample films having different thicknesses; and
   calculating the evolution of a glass transition temperature as a function of the different thicknesses.

9. The method according to claim 1, further comprising
   modulating the characteristic temperature of the sample film; and
   calculating the creep of the sample film as a function of the characteristic temperature to determine a property of the sample film, the property of the sample film being selected from the group consisting of glass transition temperature, decomposition temperature, cross-linking temperature and polymerization temperature.

10. The method according to claim 7, wherein the step of inserting the sample film between two rigid substrates includes inserting the sample film so that an area of each of the two rigid substrates that is in contact with the sample film is substantially identical.

11. A method for measuring the viscoelastic properties of a sample film, the method comprising:
    inserting the sample film sample between two rigid substrates, the sample film having a first end and a free end, the first end being fixed in a measuring device;
    applying a force on the free end of the sample film to obtain a first deformation of the sample film;
    measuring the evolution of the force to maintain the first deformation of the sample film;
    calculating a creep of the sample film using the evolution of the force;
    performing the above steps at a plurality of temperatures; and
    determining a characteristic temperature of the sample film selected from the group consisting of glass transition temperature, decomposition temperature, cross-linking temperature and polymerization temperature.

12. The method according to claim 11, wherein the step of inserting the sample film between two rigid substrates includes inserting the sample film so that an area of each of the two rigid substrates that is in contact with the sample film is substantially identical.

* * * * *